(12) United States Patent
Chou et al.

(10) Patent No.: US 7,553,957 B2
(45) Date of Patent: Jun. 30, 2009

(54) METHODS AND KITS FOR DETECTING CLASSICAL SWINE FEVER VIRUS

(75) Inventors: Chin-Sheng George Chou, Hsin (TW); Wei-Chen Chiou, Hsin (TW)

(73) Assignee: AsiaGen Corporation, Hsin-Shi (TW)

( * ) Notice: Subject to any disclaimer, the term of this patent is extended or adjusted under 35 U.S.C. 154(b) by 0 days.

(21) Appl. No.: 11/740,177

(22) Filed: Apr. 25, 2007

(65) Prior Publication Data
US 2008/0268425 A1  Oct. 30, 2008

(51) Int. Cl.
*C07H 21/04* (2006.01)
*C12P 19/34* (2006.01)
*G01N 31/22* (2006.01)

(52) U.S. Cl. ............... 536/24.32; 435/91.2; 422/61
(58) Field of Classification Search ............ None
See application file for complete search history.

(56) References Cited

U.S. PATENT DOCUMENTS 7,198,935 B1 *  4/2007  Bartosch et al. ......... 435/235.1

FOREIGN PATENT DOCUMENTS

EP  1302547  4/2003

OTHER PUBLICATIONS

Bjorklund et al., "Phylogenetic comparison and molecular epidemiology of classical swine fever virus," Virus Genes, 1999, vol. 19, No. 3, pp. 189-195.*

Fei Ye; May-Sung Li; J. David Taylor; Quan Nguyen; Heidi M. Colton; Warren M. Casey; Michael Wagner; Michael P. Weiner; and Jingwen Chen. Fluorescent Microsphere-Based Readout Technology for Multiplexed Human Single Nucleotide Polymorphism Analysis and Bacterial Identification. Human Mutation. 2001. pp. 305-316. vol. 17.

* cited by examiner

*Primary Examiner*—Kenneth R. Horlick
*Assistant Examiner*—Molly E Baughman
(74) *Attorney, Agent, or Firm*—WPAT, P.C.; Anthony King; Kay Yang

(57) ABSTRACT

The present invention provides methods and kits for detecting CSFV. The present invention also provides oligonucleotides for detecting CSFV.

18 Claims, 14 Drawing Sheets

Figure 1

One step RT-PCR
(CSFV-OUTF/CSFV-OUTR)

CSFV                    LPC

SNP nested PCR
(CSFV-SNP primer /CSFV-IR)

CSFV                    LPC
(293 bp)

Hybridization
(CSFV probe)

○                      ✗

Detection by Luminometer a. Specific fragment of Template A can be amplified.

b. Specific fragment of Template B cannot be amplified.

METHODS AND KITS FOR DETECTING CLASSICAL SWINE FEVER VIRUS

FIELD OF THE INVENTION

The invention discloses a kit for detecting classical swine fever virus (CSFV) comprising a probe, a pair of primers and a pair of SNP primers, and a method relating to polynucleotides and Megbeads probe for identifying CSFV.

BACKGROUND OF THE INVENTION

Classical swine fever (CSF) or hog cholera is a highly contagious disease of pigs and wild boars. It causes fever, skin lesions, convulsions and usually (particularly in young animals) death within 15 days. The symptoms are indistinguishable from those of African swine fever. The disease is endemic in much of Asia, Central and South America, and parts of Europe and Africa. It was believed to have been eradicated in the United Kingdom by 1966 (according to the Department for Environment, Food & Rural Affairs), but an outbreak occurred in East Anglia in 2000. It was eradicated in the USA by 1978, according to the United States Department of Agriculture. Other regions believed to be free of CSF include Australia, Canada, Ireland, New Zealand and Scandinavia. While hog cholera does not cause foodborne illness in people, economic losses to pork producers would be severe if the disease were to become established again in any countries.

The most common method of transmission is direct contact between healthy swine and those infected with hog cholera. The disease can also be transmitted through contact with body secretions and excrement from infected animals. Healthy pigs coming into contact with contaminated vehicles, pens, feed, or clothing may contract the disease. Birds, flies, and humans can physically carry the virus from infected to healthy swine. Swine owners can inadvertently cause infection through feeding their herds untreated food wastes containing infected pork scraps.

The clinical signs of hog cholera vary with the severity of the infection. There are three forms of the disease: acute, chronic, and mild.

The acute form of hog cholera is highly virulent, causing persistent fevers that can raise body temperatures as high as 107° F. Other signs of the acute form include convulsions and lack of appetite. Affected pigs will pile or huddle up together. Signs of hog cholera may not be apparent for several days following infection. Death usually occurs within 5 to 14 days following the onset of illness.

The chronic form of hog cholera causes similar clinical signs in affected swine, but the signs are less severe than in the acute form. Discoloration of the abdominal skin and red splotches around the ears and extremities often occur. Pigs with chronic hog cholera can live for more than 100 days after the onset of infection.

The mild or clinically unapparent form of hog cholera seldom results in noticeable clinical signs. Affected pigs suffer short periods of illness often followed by periods of recovery. Eventually, a terminal relapse occurs. The mild strain may cause small litter size, stillbirths, and other reproductive failures. High mortality during weaning may also indicate the presence of this mild strain of hog cholera.

Hog cholera was the most devastating disease of swine. Containment and eventual eradication required research-based information on the cause and transmission of the disease as well as methods for diagnosis and prevention.

The infectious agent is a virus, CSFV (previously called hog cholera virus) of the genus *Pestivirus* in the family Flaviviridae (or Togaviridae). CSFV is closely related to the ruminant pestiviruses which cause Bovine Viral Diarrhoea (BVDV) and Border Disease (BDV) mainly affecting cattle.

The effect of different CSFV strains varies widely, leading to a wide range of symptoms. Highly virulent strains correlate with acute, obvious disease and high mortality, including neurological symptoms and hemorrhages within the skin. Less virulent strains can give rise to subacute or chronic infections that may escape detection, while still inducing mortality in fetuses and new-borns. Infected piglets birthed from infected but subclinical sows help maintain the disease within a population. Other symptoms can include lethargy, fever, immuno-suppression and secondary respiratory infections. The incubation period of CSFV ranges from 2 to 14 days but symptoms may be apparent after 2 to 4 weeks. Animals with an acute infection can survive 2 to 3 months before their eventual death.

Eradicating CSF is problematic. Current programs revolve around rapid detection and diagnosis, and preventive culling, possibly followed by emergency vaccination. Possible sources for maintaining and introducing infection include the wide transport of pigs and pork products, as well as endemic CSF within wild boar and feral pig populations.

Vaccination of pigs with a live attenuated classical swine fever virus (CSFV) vaccine strain, particularly the "Chinese" strain (LPC, also called C-strain), protects pigs against CSF. A major drawback of vaccinating pigs with the conventional LPC vaccines, is that the vaccinated pigs cannot be distinguished serologically from pigs infected with a CSFV field strain. The LPC, however, is considered one of the most effective and safe live vaccines. Discrimination of the vaccine-strain and the infectious virulent strain would be a great improvement The genomes of pestiviruses consist of a positive strand RNA molecule of about 12.5 kb. The positive strand RNA genomes of several non-cytopathogenic BVDV strains, however, may be considerably larger.

Although less commonly available, nucleic acid testing (e.g., viral RNA or proviral DNA amplification method) can also help diagnosis in certain situations and has become more acceptable. The importance of nucleic acid testing (NAT) has become increasingly evident during the last decade for many purposes, such as diagnosing viral infections, monitoring antiviral therapy, and improving the safety of blood supplies. NAT combines the advantages of direct and highly sequence-specific detection of the genome of an infectious agent with an analytic sensitivity that is several orders of magnitude greater than that of antigen detection or virus isolation methods. NAT also reduces the risks of viral transmission during the period between infection and seroconversion, of infection with immunovariant viruses, of immunosilent carriage, and of occult carriage.

Single Nucleotide Polymorphism (SNP) is the most abundant form of genetic variation. Due to their frequency and distribution, SNPs are becoming superior genetic markers for identifying different species or virus strains. Recently, a number of methods for SNP detection have been developed, including restriction fragment length polymorphism (RFLP) analysis, single-strand conformation polymorphism analysis (SSCP), allele-specific oligonucleotide hybridization (ASO), oligonucleotide ligation as say(OLA), primer extension assay, and structure-specific flp nuclease technology. Another known method for SNP genotyping is allele-specific primer extension (ASPE). ASPE entails extension of a novel two component primer on templates which may or may not include a target nucleic acid sequence. The 3' portion of the primer is complementary to a portion of the template adjacent the target sequence. The 5' portion of the primer is complementary to a different preselected nucleic acid sequence. Extension of the 3' portion of the primer with labeled deoxynucleoside triphosphates yields a labeled extension product if, but only if, the template includes the target sequence. The presence of such a labeled primer extension product is detected by hybridization of the 5' portion to the preselected sequence as refer to Ye et al, Human mutation.17, p 305 (2001) and EP1302547A2, both of which are herein incorporated by reference in their entireties.

However, in the ASPE, it needs dCTP conjugated with biotin and extra enzymes to accomplish the reaction, wherein one is shrimp alkaline phosphotase, and the other is exonuclease I. Further, the major drawback of ASPE is that the reaction is amplified in single strand one strand at a time, in which DNA polymerase copies the DNA template, starting at the primer annealed to one of its strand, not both. Therefore, the amplification of DNA template is an arithmetic progression.

All referenced patents, applications and literatures are incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. The invention may seek to satisfy one or more of the above-mentioned desire. Although the present invention may obviate one or more of the above-mentioned desires, it should be understood that some aspects of the invention might not necessarily obviate them.

SUMMARY OF THE INVENTION

The invention provides a kit for detecting classical swine fever virus (CSFV), comprising (a) a pair of primers, SEQ ID NO.1 and SEQ ID NO. 2; and (b) a pair of SNP primers, SEQ ID NO.3 and SEQ ID NO. 4.

The invention also relates to a method for detecting CSFV comprising (a) providing an amplified cDNA of a sample by a pair of PCR primers, SEQ ID NO. 1 and SEQ ID NO. 2; (b) discriminating the amplified DNA of step (a) by a pair of SNP primers, SEQ ID NO.3 and SEQ ID NO. 4; and (c) identifying the amplified DNA of step (b) by electrophoresis or probe SEQ ID NO. 5.

The invention further provides a method for differentiating an infectious strain from a vaccine strain comprising (a) providing an amplified cDNA of a sample by a pair of PCR primers sharing the same template from the infectious and vaccine strains; (b) discriminating the amplified DNA of step (a) by a pair of SNP primers which is incompletely complementary to the amplified DNA in step (a); and (c) identifying the size of the amplified DNA of step (b) by electrophoresis or probe hybridized with the amplified DNA of step (b) from the infectious strain or the vaccine strain.

BRIEF DESCRIPTION OF THE DRAWINGS

FIG. 1 shows the outline of the detection method of invention.

Figure 3:
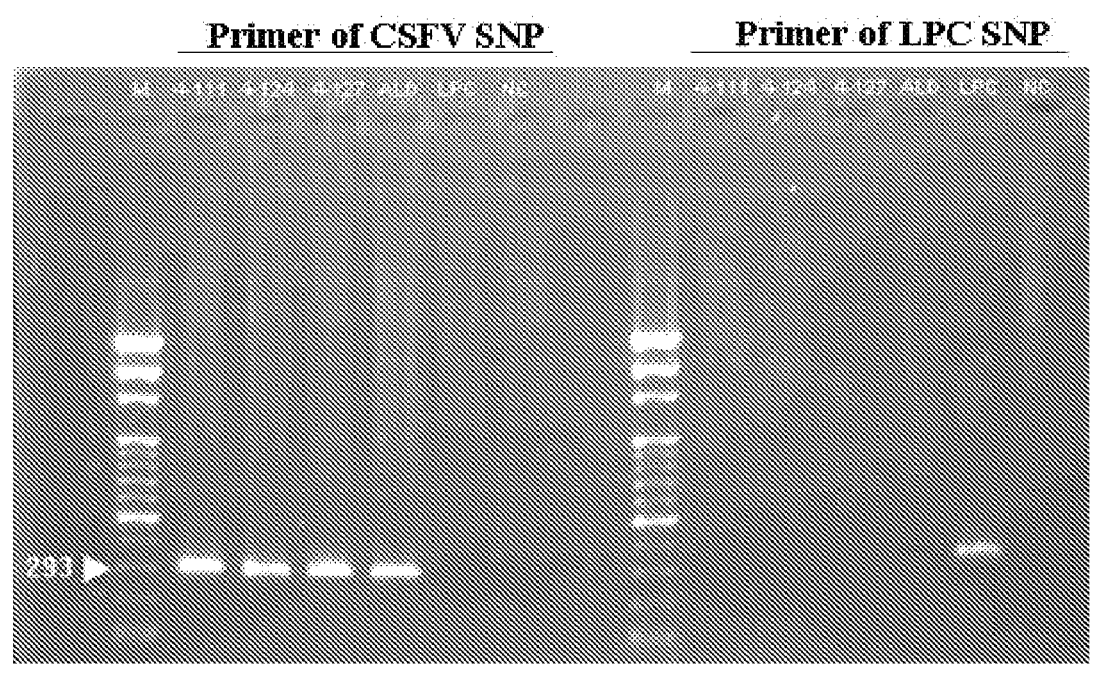

FIG. 3 shows the electrophoresis result of SNP nested PCR. Using different specific SNP primers to discriminate classical swine fever virus (CSFV) vaccine strain LPC and other infectious virulent strain. NC: negative control; bp: base pair. LPC indicates the CSFV vaccine strain; 4-111 ` 4-124 ` 4-127 are three selected from wild weak CSFV strains. ALD indicates the strong infectious CSFV strain.

Figure 4:
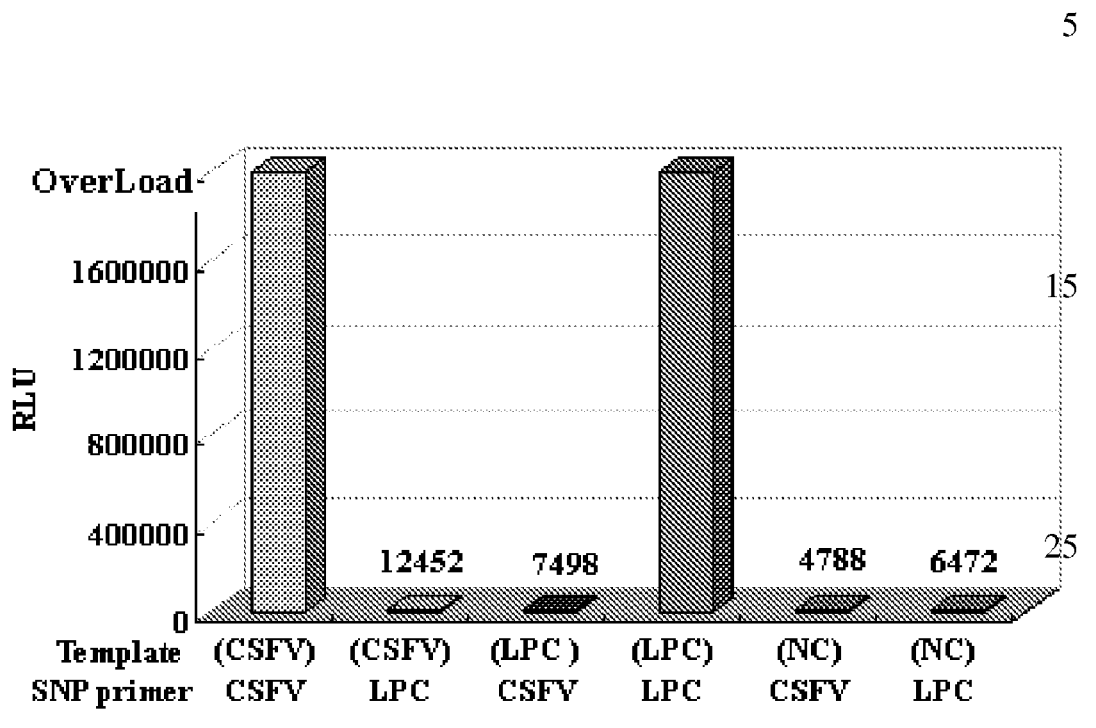

FIG. 4 shows the detection result of CSFV SNP nested PCR product by luminometer. Overload means that RLU value is over 2 million.

NC: negative control; bp: base pair. LPC indicates the CSFV vaccine strain; Overload means that RLU value is over 2 million.

Figure 13:
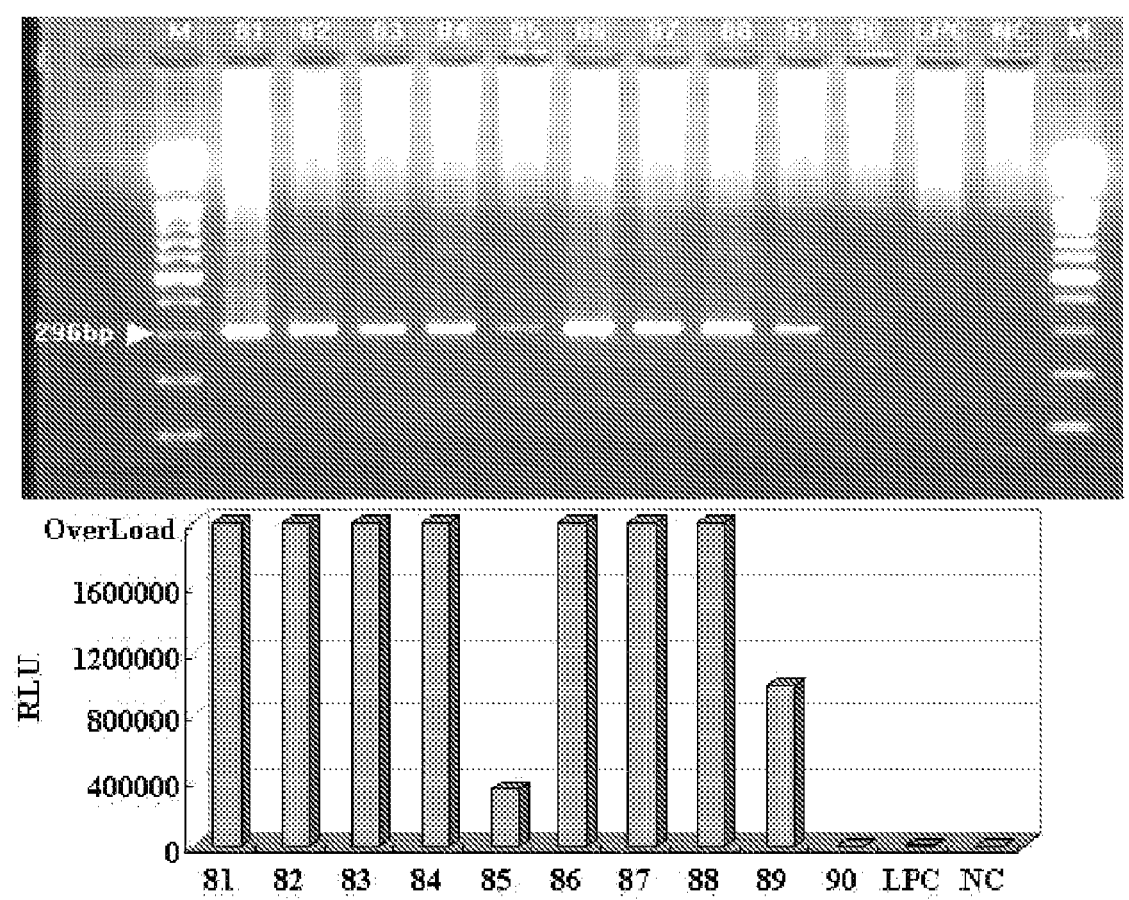

FIG. 13 shows the identification of CSFV from number 81 to 90 clinical CSFV samples by the assay of the invention and discriminate CSFV from its vaccine strain (LPC). Upper panel is the electrophoresis result of SNP nested PCR. Lower panel is the detection result of PCR product by luminometer. NC: negative control; bp: base pair. LPC indicates the CSFV vaccine strain; Overload means that RLU value is over 2 million.

Figure 14:
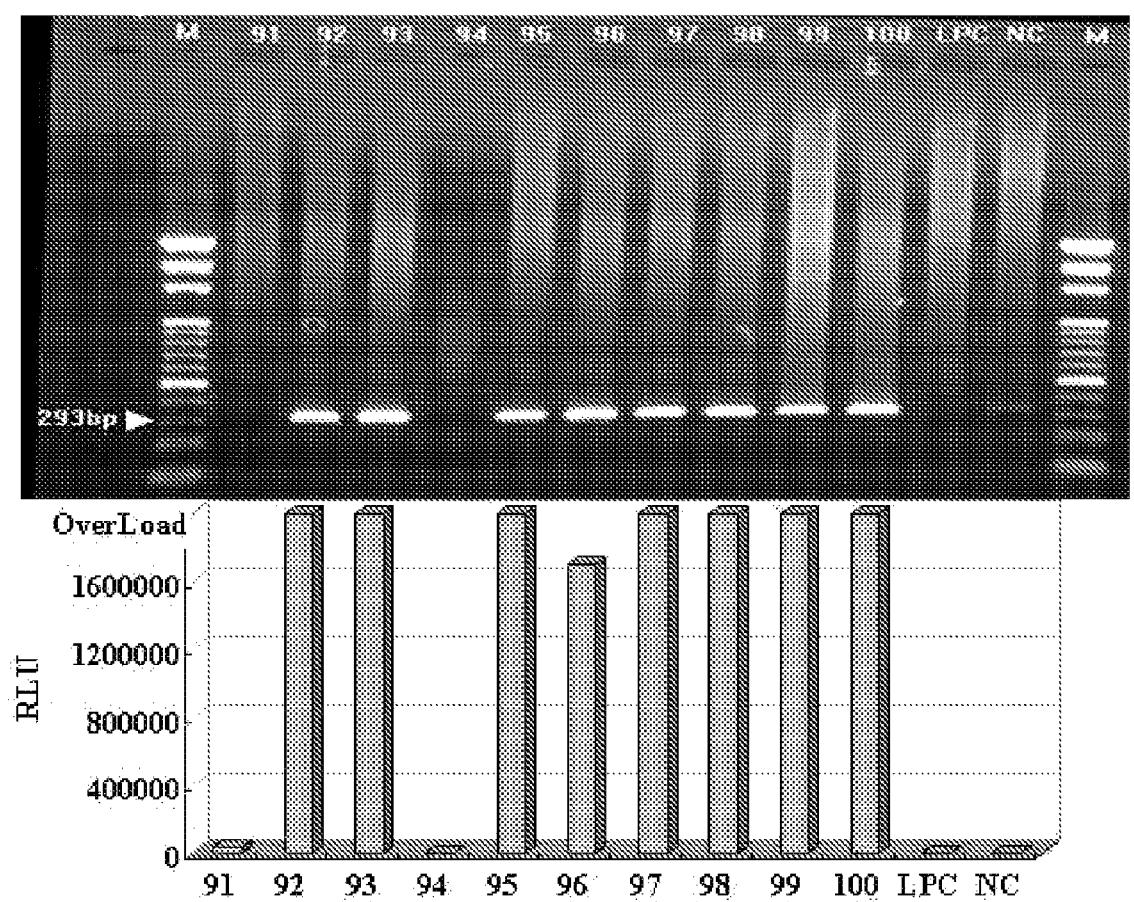

FIG. 14 shows the identification of CSFV from number 91 to 100 clinical CSFV samples by the assay of the invention and discriminate CSFV from its vaccine strain (LPC). Upper panel is the electrophoresis result of SNP nested PCR. Lower panel is the detection result of PCR product by luminometer. NC: negative control; bp: base pair. LPC indicates the CSFV vaccine strain; Overload means that RLU value is over 2 million.

DETAILED DESCRIPTION OF THE INVENTION

Hog cholera or classical swine fever (CSF) was the most severe disease of swine, causing devastating losses. CSF is a highly contagious disease of pigs and endemic in much of Asia, Central and South America, and parts of Europe and Africa. Eradicating CSF is problematic. Current programs revolve around rapid detection and diagnosis, and preventive culling, possibly followed by emergency vaccination. Vaccination of pigs with a live attenuated classical swine fever virus (CSFV) vaccine strain, the "Chinese" strain, LPC (also called C-strain), protects pigs against CSF.

However, in the region where LPC vaccine is given, one major problem of hog cholera prevention is CSFV detection. Although LPC is considered one of the most effective and safe live vaccines, LPC vaccinated pigs cannot be distinguished from the pigs infected with a CSFV field strain. Epidemic prevention of CSF is gradually out of control as a consequence of CSFV detection interfered with LPC vaccine strain, especially in the mild or clinically unapparent affected pigs. To overcome this problem, the present invention improves the current method of detection, as shown in FIG. 1, which outlines the detection method of the contemplated invention. It offers a more effective, more rapid, and more sensitive kit and method to detect CSFV in order to control the epidemic situation as soon as possible. And through this, the existence of CSFV can be easily diagnosed without interference from the LPC vaccine strain. The invention provides oligonucleotides, methods for amplifying and detecting CSFV, and kits comprising these oligonucleotides.

In the present invention, a concept of single nucleotide polymorphism(SNP) combined with nested DNA polymerase chain reaction named SNP nested PCR, which has been developed to amplify specific allele to examine abundant SNP markers or to discriminate different virus variations at a time. The advantages of present invention includes: (1) only DNA polymerase is needed without extra enzymes or labeled deoxynucleoside triphosphates.(2) DNA polymerase copies the DNA template, starting at the primers annealed to both of its strand. Therefore, the amplification of DNA template is a geometric progression.

Accordingly, this invention provides a kit comprising a pair of PCR primers, and a pair of SNP nested PCR primers.

In one embodiment, the pair of PCR primers, i.e., a forward oligonucleotide and a reverse oligonucleotide for amplifying a nucleic acid of CSFV, the forward one comprises (i) a nucleic acid sequence selected from the nucleic acid sequence of SEQ ID NO.1 and (ii) a nucleic acid sequence fully complementary to the nucleic acid sequence of (i); the reverse one comprises (iii) a nucleic acid sequence selected from the nucleic acid sequence of SEQ ID NO.2 and (iv) a nucleic acid sequence fully complementary to the nucleic acid sequence of (iii). The pair of SNP nested PCR primers, i.e., an forward oligonucleotides for amplifying target allelic and improving sensitivity, and a reverse oligonucleotide for amplifying a nucleic acid of CSFV, the forward SNP primer comprises (v) a nucleic acid sequence selected from the nucleic acid sequence of SEQ ID NO.3, and (vi) a nucleic acid sequence full complementary to the nucleic acid sequence of (v); the reverse one comprises (vii) a nucleic acid sequence selected from the nucleic acid sequence of SEQ ID NO.4 and (viii) a nucleic acid sequence full complementary to the nucleic acid sequence of (vii). And the probe, i.e., an oligonucleotides for detecting the nucleic acid of CSFV, comprises (ix) a nucleic acid sequence selected from the nucleic acid sequence of SEQ ID NO.5 and (x) a nucleic acid sequence full complementary to the nucleic acid sequence of (ix).

In a preferred embodiment, the probe is labeled with a magnetic particle. And, the magnetic particle labeled on the probe is coupled by a coupling agent comprising 1-ethyl-3-(3-dimethylaminopropyl) cobodiimide (EDC).

In addition to the primers of the present invention, the kit of the present invention further comprises dNTP, Taq DNA Polymerase, RNase inhibitor, ddH$_2$O and extension buffer.

The extension buffer used in the present invention includes, but not limited to, Tris-HCl, MgCl$_2$ and KCl.

In another embodiment, a method for differentiating an infectious strain from a vaccine strain comprising (a) providing an amplified cDNA of a sample by a pair of PCR primers sharing the same template from the infectious and vaccine strains; (b) discriminating the amplified DNA of step (a) by a pair of SNP primers which is incompletely complementary to the amplified DNA in step (a); and (c) identifying the size of the amplified DNA of step (b) by electrophoresis or probe hybridized with the amplified DNA of step (b) from the infectious strain or the vaccine strain.

In a preferred embodiment, the incompletely complementary to the amplified DNA is caused by protruding and unbinding nucleotides. The protruding and unbinding nucleotides between the un-complementary binding of the SNP primer and the amplified DNA of the infectious strain in step (a) are distributed at one, two or three areas.

In a more preferred embodiment, the protruding and unbinding nucleotides between the un-complementary binding of the SNP primer and the amplified DNA of the vaccine strain is distributed at three areas.

The term "nucleic acid" as used herein, refers to a deoxyribonucleotide or ribonucleotide polymer in either single- or double-stranded form, and unless otherwise limited, would encompass analogs of natural nucleotide that function in a similar manner as naturally occurring nucleotide. Nucleic acids may be cloned or synthesized using any technique known in the art.

The term "complementary" as used herein, refers to the natural binding of nucleotides under permissive salt and temperature conditions by base-pairing. For example, the sequence "A-G-T" binds to the complementary sequence "T-C-A." Complementarity between two single-stranded molecules may be "partial," in which only some of the nucleic acids bind, or it may be complete when the total complementarity exists between the single stranded molecules. The degree of complementarity between nucleic acid strands has significant effects on the efficiency and strength of hybridization between nucleic acid strands.

The polymerase chain reaction (PCR) and other forms of target amplification have enabled rapid advances in the development of powerful tools for detecting and quantifying specific DNA sequence of interest for research, forensic and clinical applications. As used herein, RT-PCR (reverse transcription polymerase chain reaction) is a technique for amplifying a defined piece of a ribonucleic acid (RNA) molecule extracted from clinical samples. The RNA strand is first reverse transcribed into its DNA complement or complementary DNA, followed by amplification of the resulting DNA using polymerase chain reaction.

To ensure the specificity of PCR, the nested PCR is further performed in this method. Nested PCR means that two pairs of PCR primer were used for a single locus. The first primer pair, also called outer primers, was performed in RT-PCR to amplify the target locus. The second pair of primers (nested, inner primers) binds within the first PCR product and produces a second PCR product that will be shorter than the first one. The logic behind this strategy is that if the non-specific locus were amplified by mistake in the first PCR reaction, the probability is very low that it would also be amplified a second time by a second pair of primers.

The steps of selecting and analyzing process are resulted with the use of bio-information software, primer primer 5, BCM net (http://searchlauncher.bcm.tmc.edu/), and BOX-SHADE3.21 (http://www.ch.embnet.org/software/BOX_form.html). The software is used for the primer and probe design, which is not only for specifically target to wanted region, but also to avoid complementary binding within primers and probe such as a hairpin structure, which refers to a stem and loop association of nucleotides with a palindromic sequence that causes them to form hydrogen bonds with their complementary nucleotides on the same strand.

Because CSFV is a single strand RNA virus, with a highly mutation rate and varieties, the detection of CSFV will be affected by ELISA or some poorly designed NAT methods. To avoid this problem, the present invention has the primer design region located at NS5B in CSFV virus genome, owing to its slightly variation and lowest mutation rate. After CSFV infects host, NS5B is the first transcribed gene. The product of NS5B, a RNA-dependent RNA polymerase (RdRP), is an important protein for replicating the virus genome. It does not only help the CSFV virus genome from single strand to double strands, but also assist the translation of virus protein and later processing, in order to form some structural protein, like p 14, gp44/48 (ERNS), gp33 (E1), and gp55 (E2). Therefore, in evolution, to ensure the function of NS5B, it is very important to maintain NS5B gene sequence stability.

Figure 2:
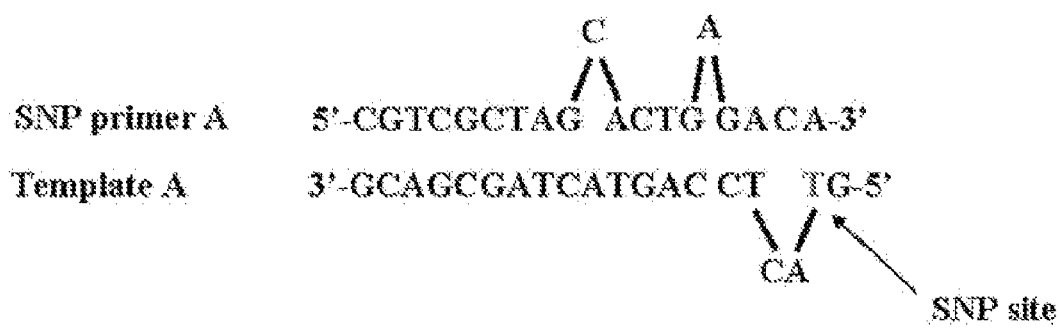
FIG. 2 shows the basic principle of SNP primer design.
Figure 2:
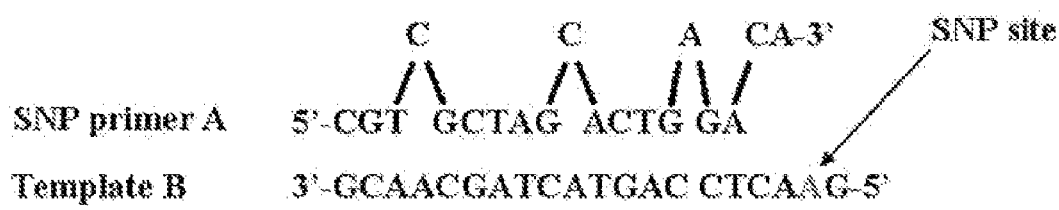
Figure 5:
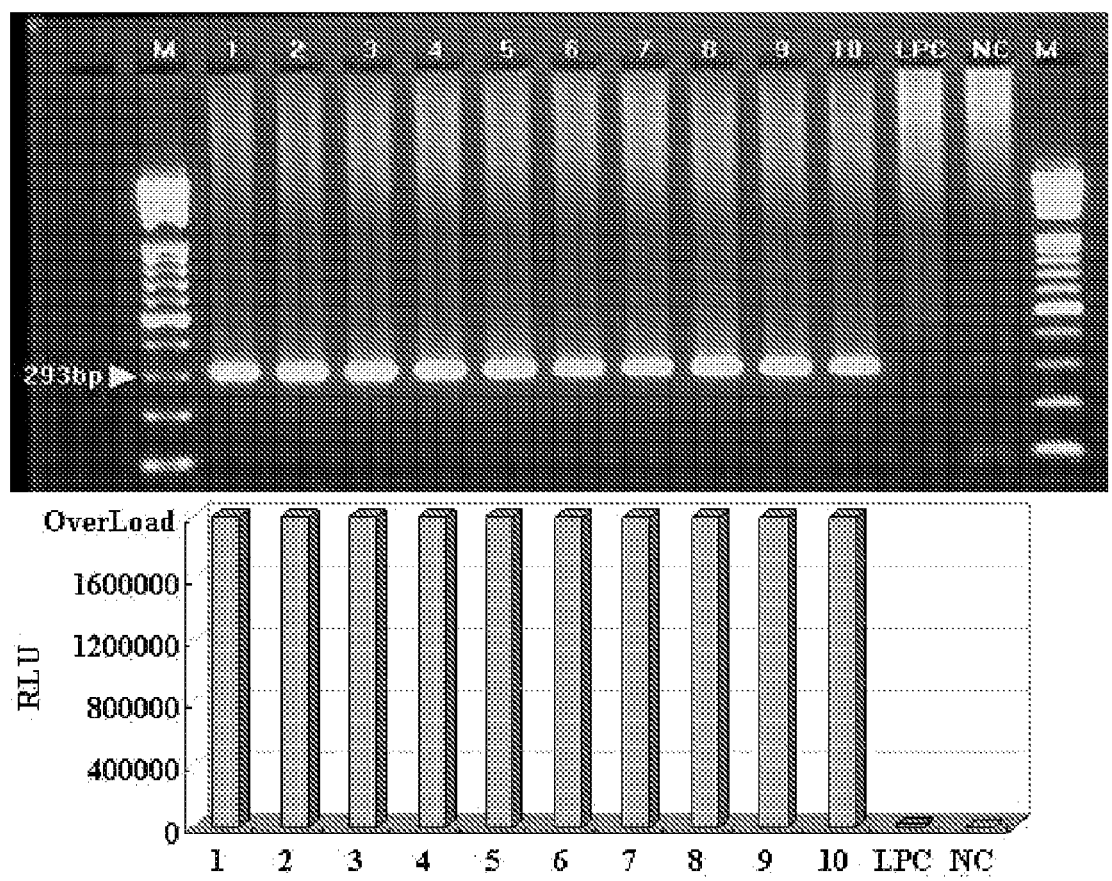
FIG. 5 shows the identification of CSFV from number 1 to 10 clinical CSFV samples by the assay of the invention and discriminate CSFV from its vaccine strain (LPC). Upper panel is the electrophoresis result of SNP nested PCR. Lower panel is the detection result of PCR product by luminometer. NC: negative control; bp: base pair. LPC indicates the CSFV vaccine strain; Overload means that RLU value is over 2 million.
Figure 6:
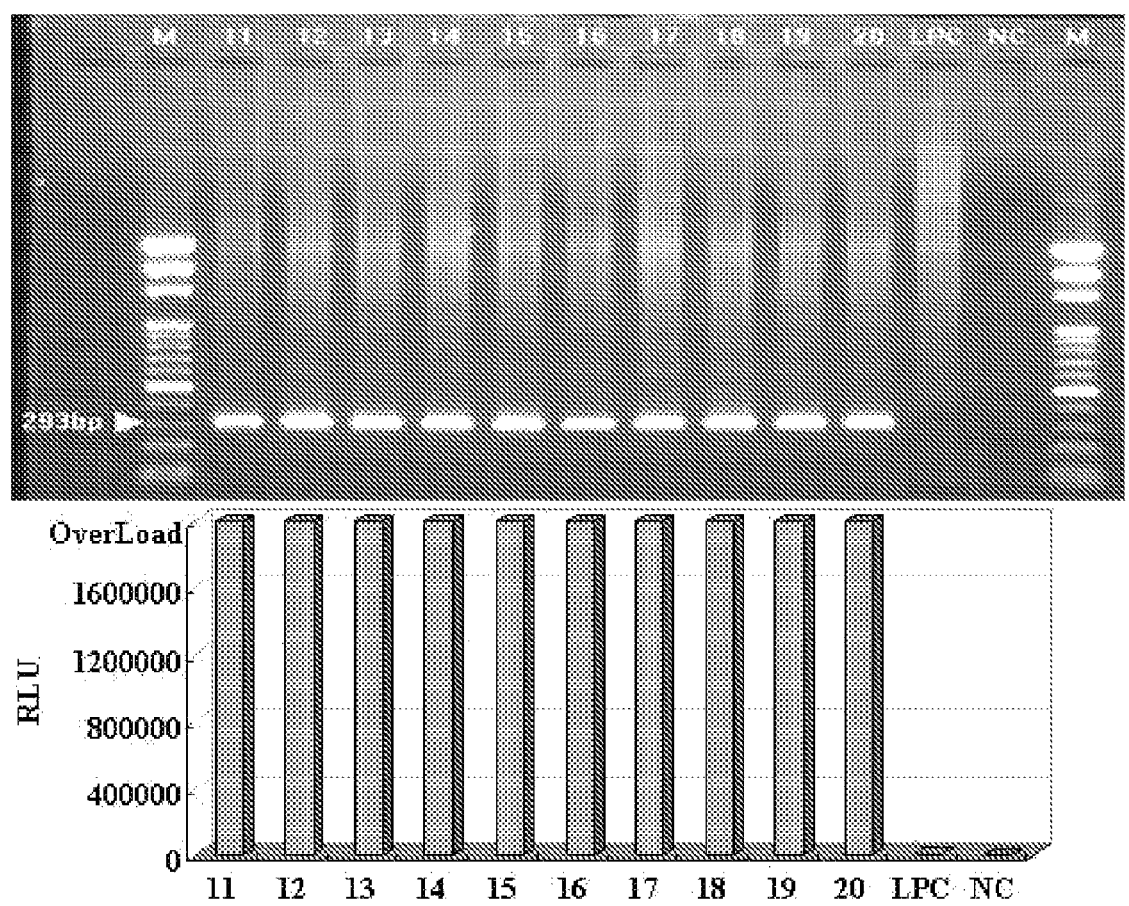
FIG. 6 shows the identification of CSFV from number 11 to 20 clinical CSFV samples by the assay of the invention and discriminate CSFV from its vaccine strain (LPC). Upper panel is the electrophoresis result of SNP nested PCR. Lower panel is the detection result of PCR product by luminometer. NC: negative control; bp: base pair. LPC indicates the CSFV vaccine strain; Overload means that RLU value is over 2 million.
Figure 7:
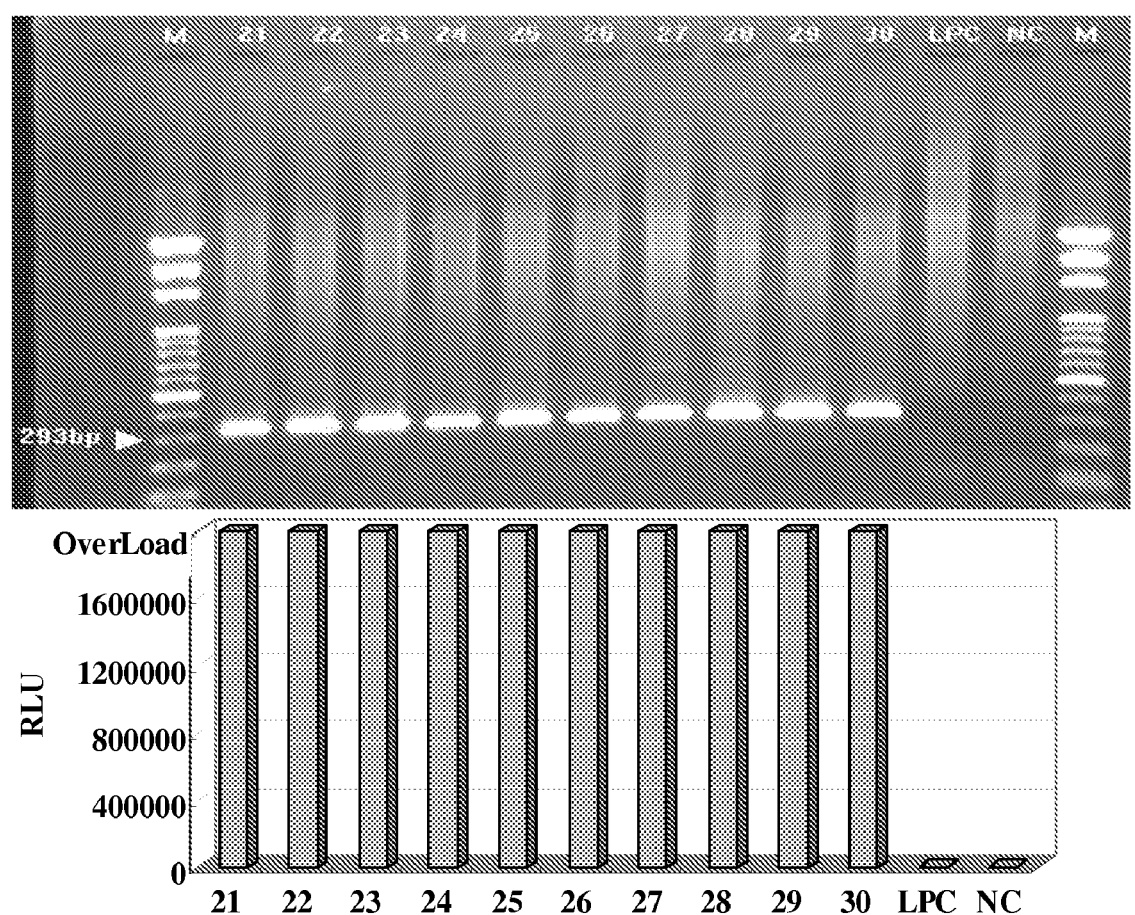
FIG. 7 shows the identification of CSFV from number 21 to 30 clinical CSFV samples by the assay of the invention and discriminate CSFV from its vaccine strain (LPC). Upper panel is the electrophoresis result of SNP nested PCR. Lower panel is the detection result of PCR product by luminometer. NC: negative control; bp: base pair. LPC indicates the CSFV vaccine strain; Overload means that RLU value is over 2 million.
Figure 8:
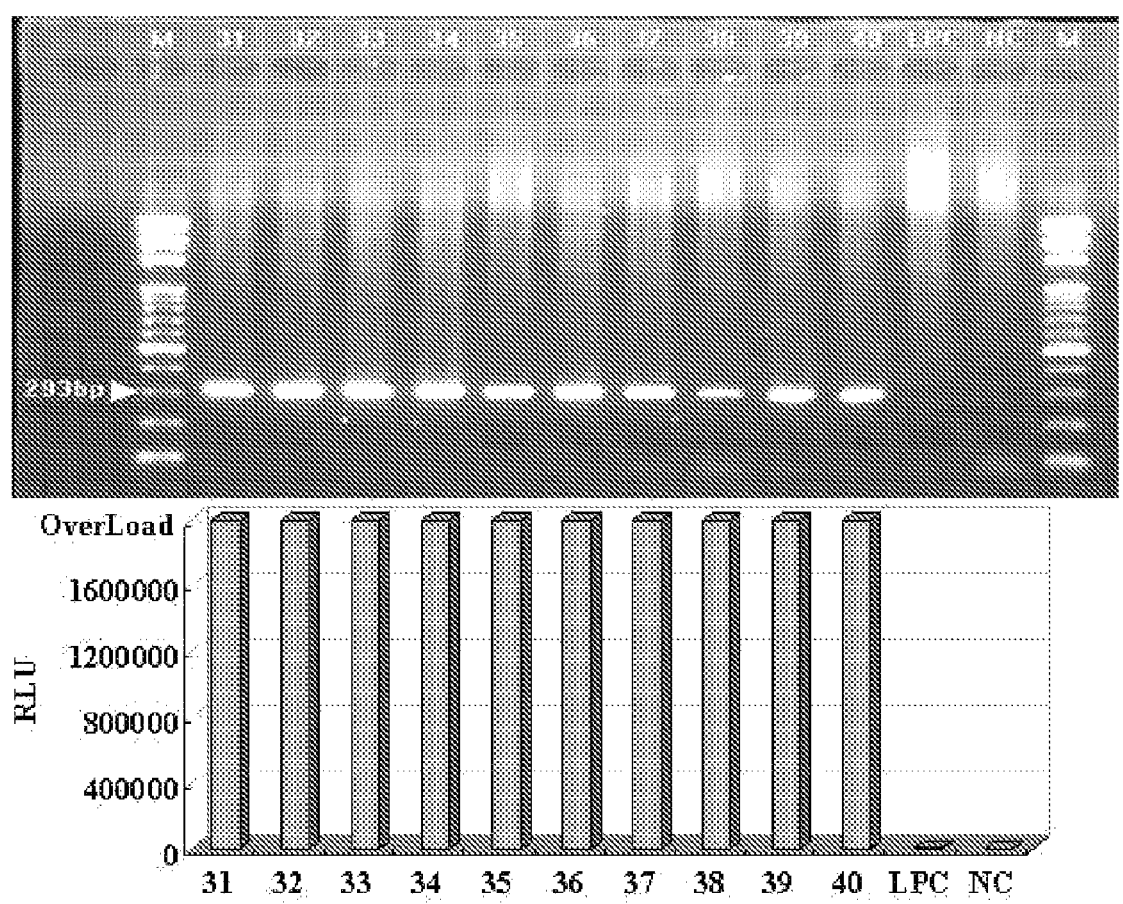
FIG. 8 shows the identification of CSFV from number 31 to 40 clinical CSFV samples by the assay of the invention and discriminate CSFV from its vaccine strain (LPC). Upper panel is the electrophoresis result of SNP nested PCR. Lower panel is the detection result of PCR product by luminometer. NC: negative control; bp: base pair. LPC indicates the CSFV vaccine strain; Overload means that RLU value is over 2 million.
Figure 9:
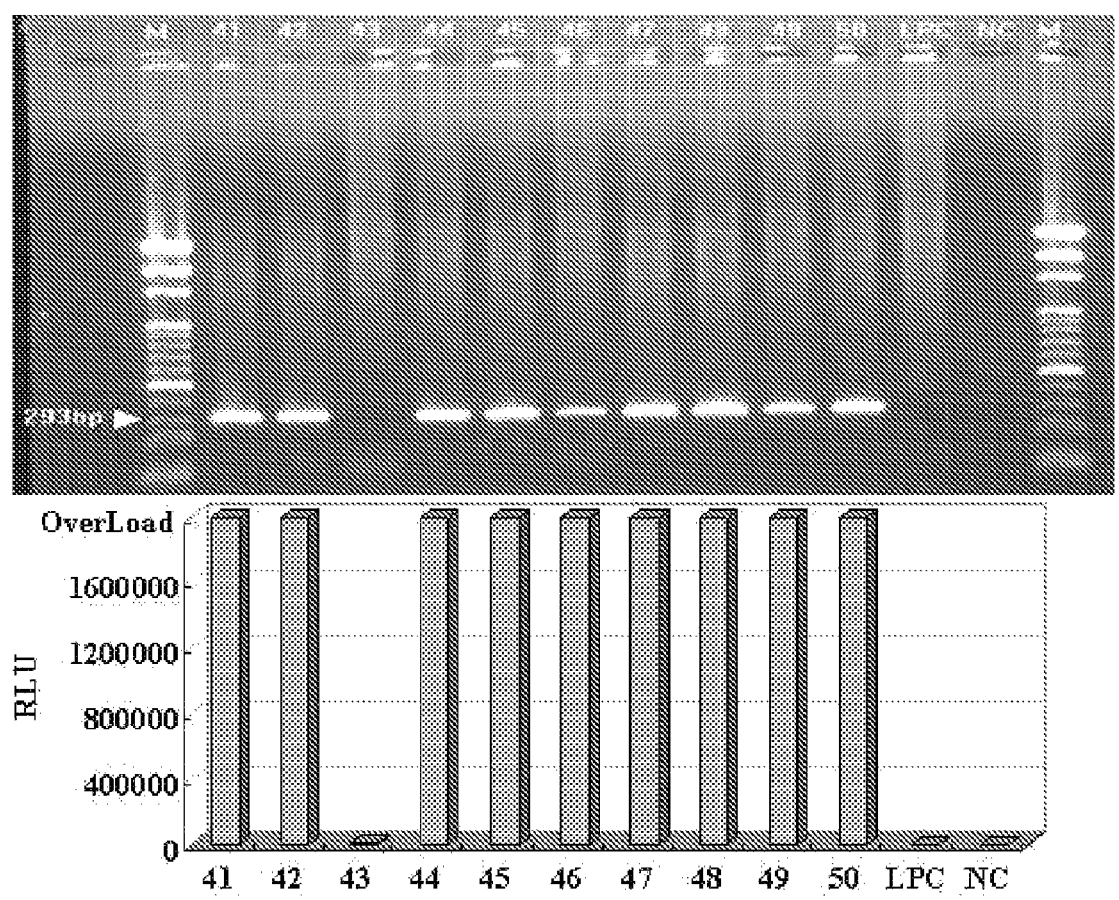
FIG. 9 shows the identification of CSFV from number 41 to 50 clinical CSFV samples by the assay of the invention and discriminate CSFV from its vaccine strain (LPC). Upper panel is the electrophoresis result of SNP nested PCR. Lower panel is the detection result of PCR product by luminometer. NC: negative control; bp: base pair. LPC indicates the CSFV vaccine strain; Overload means that RLU value is over 2 million.
Figure 10:
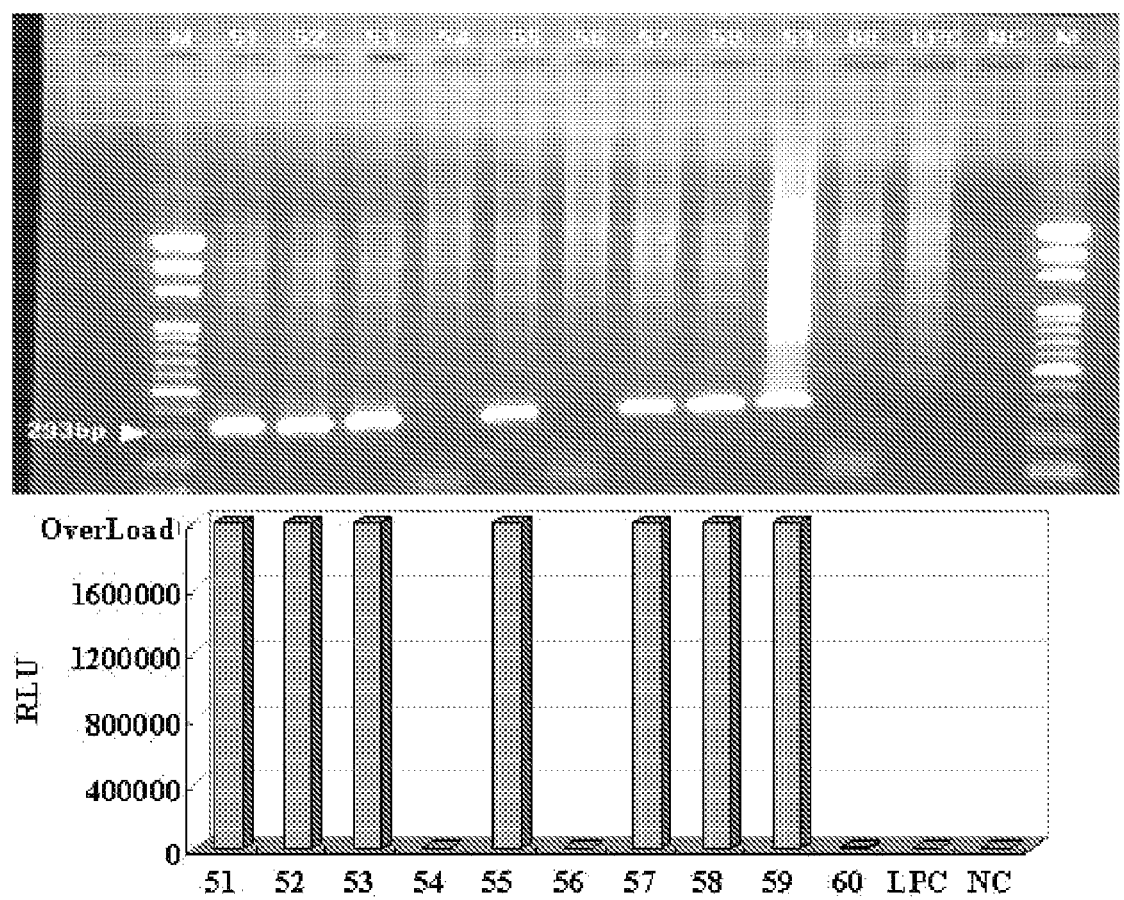
FIG. 10 shows the identification of CSFV from number 51 to 60 clinical CSFV samples by the assay of the invention and discriminate CSFV from its vaccine strain (LPC). Upper panel is the electrophoresis result of SNP nested PCR. Lower panel is the detection result of PCR product by luminometer. NC: negative control; bp: base pair. LPC indicates the CSFV vaccine strain; Overload means that RLU value is over 2 million.
Figure 11:
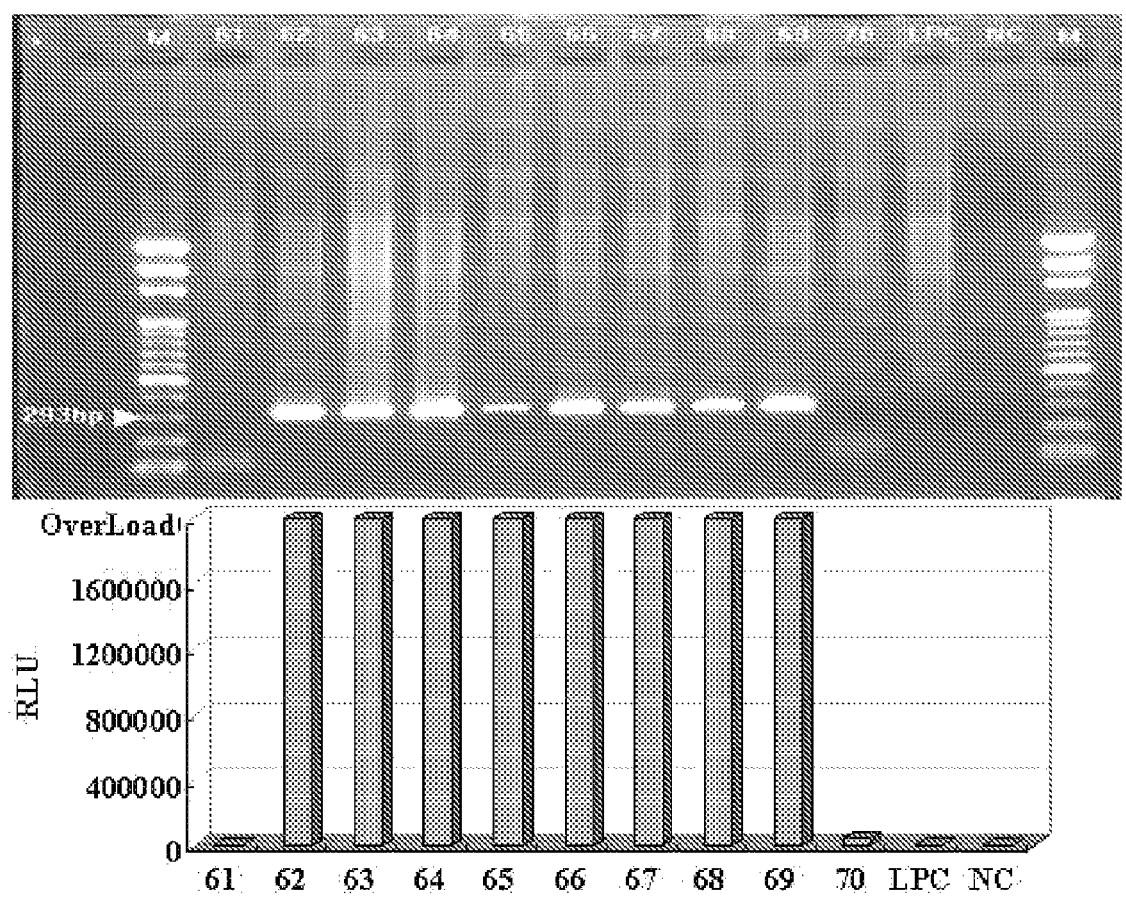
FIG. 11 shows the identification of CSFV from number 61 to 70 clinical CSFV samples by the assay of the invention and discriminate CSFV from its vaccine strain (LPC). Upper panel is the electrophoresis result of SNP nested PCR. Lower panel is the detection result of PCR product by luminometer. NC: negative control; bp: base pair. LPC indicates the CSFV vaccine strain; Overload means that RLU value is over 2 million.
Figure 12:
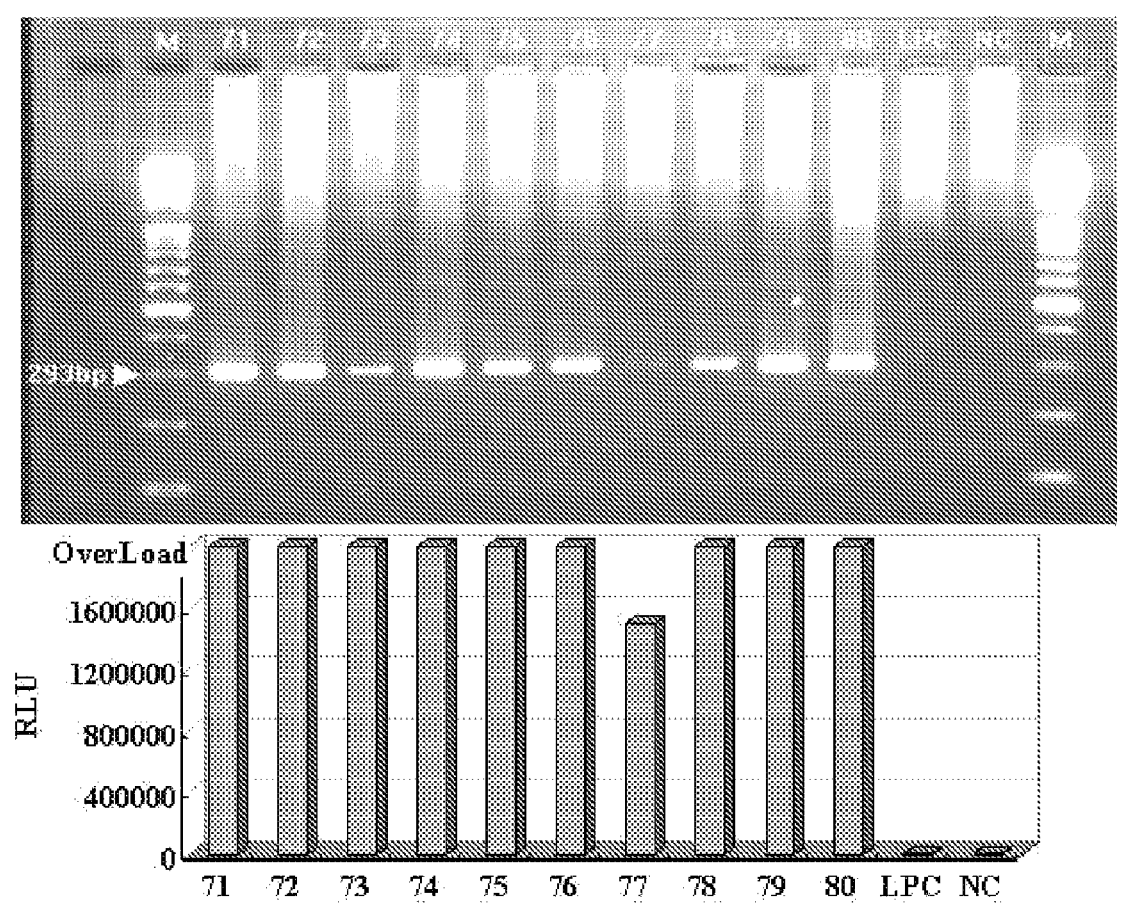
FIG. 12 shows the identification of CSFV from number 71 to 80 clinical CSFV samples by the assay of the invention and discriminate CSFV from its vaccine strain (LPC). Upper panel is the electrophoresis result of SNP nested PCR. Lower panel is the detection result of PCR product by luminometer.

In the present invention, as shown in FIG. 2, the concept is to use SNP to detect and discriminate different nucleic acid sequences. For example, in FIG. 2a, the SNP primer A is not completely complementary to template A, but the bubbles (protruding and unbinding nucleotides) between SNP primer A and template A will not impede the DNA polymerase reaction. Thus, the specific fragment of template A can be amplified. However, in FIG. 2b, the bubbles between SNP primer A and template B is too many for DNA polymerase to exert its function. The presented invention is based on this principle to design SNP primer, in order to discriminate classical swine fever virus (CSFV) vaccine strain and other infectious virulent strain.

In the present invention, a concept of above SNP primer design combined with nested DNA polymerase chain reaction named SNP nested PCR, which has been developed to amplify the specific allele to examine the abundant SNP markers or discriminate different virus variations at a time. In preferred embodiments, the present invention has overcome the following problems: (1) Using SNP primer design to avoid the noise signal from LPC vaccine strain. (2) SNP primer design is specific to NS5B gene region, to ensure the accuracy and high affinity of virus detection. (3) Using nested PCR to enhance the sensitivity of virus detection.

The amplification product produced as above can be detected during or subsequently to the amplification of the target sequence. Gel electrophoresis can be employed to detect the products of an amplification reaction after its completion. Alternatively, one or more of the primers or dNTPs used in the amplification reactions can be labeled so that an amplicon can be directly detected by conventional techniques subsequently. For example, amplification products are hybridized to probes then separated from other reaction components and detected using micro-particles and labeled probes. Many detection techniques have been developed recently, and their quantifications are generally achieved by measuring the specifically activity of the labeled capture probe, in which enzymes are often employed as biocatalytic labels for the amplified detection of DNA-sensing events.

To facilitate CSFV detection, the present invention also provides a Magbeads probe for detecting CSFV, comprising an oligonucleotide for detecting CSFV and magnetic beads (Magbeads).

In one embodiment, a method for detecting classical swine fever virus (CSFV) comprises (a) providing an amplified cDNA of a sample by a pair of PCR primers, SEQ ID NO.1 and SEQ ID NO. 2; (b) discriminating the amplified DNA of step (a) by a pair of SNP primers, SEQ ID NO.3 and SEQ ID NO. 4; and (c) identifying the amplified DNA of step (b) by electrophoresis or probe SEQ ID NO. 5.

In a preferred embodiment, the SNP primer SEQ ID NO.3 is incompletely complementary to the amplified DNA. The incompletely complementary to the amplified DNA is caused by protruding and unbinding nucleotides. The protruding and unbinding nucleotides between the un-complementary binding of SNP primer SEQ ID NO.3 and the amplified DNA of CSFV infectious virulent strain is distributed at one, two or three areas.

In a further preferred embodiment, 293 base pairs was amplified in a SNP nested DNA polymerase chain reaction. The product can be identified by electrophoresis or probe SEQ ID NO.5. The SNP nested PCR primer SEQ ID NO.3 is linked to biotin, wherein the biotin is linked to an enzyme for luminescent substrate. The enzyme is horseradish peroxidase. The method further comprises measuring luminescence by adding luminescent substrate.

The blocking solution used in the present invention comprises, but not limited to, casein.

The enzyme reagent used herein comprises, but not limited to, streptavidin-horseradish peroxidase.

The luminescent substrate as used herein refers to $H_2O_2$ and luminol.

In general, any body fluid such as CSF, serum, blood, sputum, pleural effusion, throat swab and stools can be used in the clinical tests. The preferred samples for this invention are from CSF, serum, blood, sputum, pleural effusion, and throat swab.

The term "sample" as used herein, is used in its broadest sense. A biological sample suspected of containing nucleic acid encoding CSFV, or fragments thereof may comprise a body fluid, extract from a cell, chromosome, organelle, or membrane isolated from a cell, genomic DNA, RNA, or cDNA (in solution or bound to a solid support, a tissue, a tissue print, and the like).

As used herein, a "probe" is a substance that can specifically recognize a particular target. Generally, probes will be attached on solid support to facilitate the separation of DNA. In the present invention, the probes linked to magnetic beads are preferred. Magnetic beads covalently coupled to amine-containing oligonucleotides through their carboxylate groups on the surface. The small size allows the magnetic beads to remain in suspension for several hours, which is more sufficient for assay setup and analysis, and also provides near-fluid-phase reaction kinesis.

The term "hybridization" as used herein, refers to any process by which a strand of nucleic acid binds with a complementary strand through base pairing to form a hybridization complex between two nucleic acid sequences by virtue of the formation of hydrogen bonds between complementary G and C bases and between complementary A and T bases. These hydrogen bonds may be further stabilized by base stacking interactions. The two complementary nucleic acid sequences hydrogen bond are in an antiparallel configuration. A hybridization complex may be formed in a solution and another nucleic acid sequence immobilized on a solid support (e.g., paper, membranes, filters, chips, pins, glass slides, or any other appropriate substrates to which cells or their nucleic acids have been fixed).

Commonly employed labels include, but are not limited to, biotin, fluorescent molecules, radioactive molecules, chromogenic substrates, chemi-luminescence, and the like. In this present invention, the nucleic acid or oligonucleotide labeled biotin is preferred. When biotin is employed, it is detected by avidin, streptavidin or the like, which is conjugated to a detectable marker, such as an enzyme (e.g., horseradish peroxidase).

For convenient utilization, the primers and probes are labeled with detectable component or molecules. The probe is labeled with a magnetic particle as a magnetic probe. The primer, including forward primer, reverse primer or both, is labeled by a bioactive component such as biotin. The amplified DNA product hybridized with magnetic probe forming a hybrid complex, and this hybrid complex has affinity with a magnetic material, so that the hybrid complex can be easily separated from unbound DNA products by using a magnetic rack. The hybrid complex can be further quantified by using the labeled primer. For example, if the primer is labeled with biotin, avidin, the substrate of biotin, will be added into the isolated hybrid complex. The hybrid complex can be further quantified by Luminometer.

EXAMPLES

Material and Methods

Major kit A: (50 reactions/kit, store in room temperature).
(1) Hybridization buffer (1500 μl per bottle, 2 bottles).

Major kit B: (50 reactions/kit, store at 2~8° C.).
(1) Detection solution (1500 μl per bottle, 2 bottles).
(2) Magnetic probe (180 μl per bottle, 1 bottle). CSFV probe, magnetic beads number: 3 CSFV probe (SEQ ID NO: 5): amin-TAGAAGTGTTGTCTGACCACCTTACTTG-TATTGG Major kit C: (50 reactions/kit, store at −20±5° C.)
(1) Nucleotide amplification solution 1 (420 μl per bottle, 5 bottles, store at −20±5° C.)

```
DEPC, H2O

CSFV outer forward primer (5 μM)
TGTTAACAATGGTTTACGCCTGCTGCGAG

CSFV outer reverse primer (5 μM)
GTGGTTGACTTGCCTGGTTTCACTTGCGGTT
```

```
                    -continued
10 x polymerase buffer (Hot start: JMR-470)

dNTP(A ' U ' C ' G) (10 mM)

MgCl2 (25 mM)
```

(2) Nucleotide amplification solution 2 (420 μl per bottle, 5 bottles, store at −20±5° C.)

```
DEPC, H2O

CSFV-SNP forward primer (5 μM)
AGAAATTGGCGAGTAAAGGA GGCCAGATCCTA

CSFV inner reverse primer (5 μM)
TCTGATTAGTGGGTTCCAGG ATTACATCAGC 10 x polymerase buffer (Hotstar: JMR-470)

dNTP (A ' U ' C ' G).

MgCl2 (25 mM)
```

(3) Reverse transcriptase (5.5 μl per bottle, 1 bottle, store at −20±5° C.)
(4) RNase inhibit enzyme (27 μl per bottle, 1 bottle, store at −20±5° C.)
(5) Polymerase (11 μl per bottle, 1 bottles, store at −20±5° C.)

Example 1

Analysis of Nucleotide Sequence and Design of Primers and Probes

Collecting and integrating the genomic sequence which has already been identified. Further, compared and analyzed by use of bio-information software primer primer 5, BCM net (http://searchlauncher.bcm.tmc.edu/), and BOXSHADE3.21 (http://www.ch.embnet.org/software/BOX_form.html), both of which are herein incorporate by reference in their entireties. In NS5B region, it is considered to select and design a target fragment as primer or probe having the sequences which are characteristic and specific for identifying CSFV virus. The CSFV SNP primer is specifically designed to discriminate the wild infectious CSFV strain and CSFV vaccinated strain. The basic principle is shown as in FIG. 2: Analyze and cross compare the chosen probe and primer sets all together to avoid primer dimmer or hairpin. Further, the step was needed to check the chosen probe and primer sets along with other varied viruses genomes to avoid nonspecific identification.

Example 2

Establish Methods of Clinical Sample Treatment

The primarily test sample, as serum or Buffy coat, was applied to RNA extraction for processing RT-PCR reaction. This step examines different extraction methods in order to simplify the extraction procedures.

Example 3

Study of the Clinical Sampling

Study and survey the clinical samples to choose the best moment and objects for sampling. The objects could be piglet, sows or hogs.

Example 4

Establishment and Optimization of Nuclei Acid Amplification 4.1 First, establish PCR condition for CSFV detection: Established the CSFV sensitivity analysis and compared parallel with real time PCR, using the same serum sample to quantify. This sample could be further used as a control for clinical sample sensitivity analysis. In these experiments, the reverse transcriptions reacted in the same condition.

4.2 Establish the internal standard: This step was used to confirm and distinguish the negative and pseudo-positive results. The quantified internal standard put into the serum sample had been through the process of extraction, reverse transcription, and nuclei acid amplification, in order to coordinate with the best reaction condition of CSFV RT-PCR.

Example 5

Establishment and Optimization of SNP Nested PCR

The present invention provides a more sensitive method for detecting CSFV. The key is the process of SNP nested PCR. The product of RT-PCR as the template, the SNP primer SEQ ID NO.3 linked biotin as the forward primer, the CSFV inner reverse primer SEQ ID NO.4, DNA polymerase and dNTPs were added, and specific fragments were selected and amplified by the method of SNP nested PCR. As a result, the interested fragments were selected and amplified to improve the sensitivity of the detection. As shown in FIG. 3, it is the electrophoresis result of SNP nested PCR. Different specific SNP primers is used to discriminate classical swine fever virus (CSFV) vaccine strain and other infectious virulent strain.

Example 6

Examine the Optimal Conditions of CSFV Probe and Hybridization Reactions

The present invention provided a probe of SEQ ID NO.5, and got the result of RT-PCR and SNP nested PCR through these probes. The whole reaction was performed with one step method and based on liquid hybridized reaction. The major affected factors of hybridized reaction was under investigation, including the salt concentration, kinds and concentration of detergents, reaction temperature, reaction time, and combination of these four factors with the probes to see whether there are cross interferences or signals. Test of the diluted detection buffer to lower down the number of kit need. The goal of this work is to find the optimal hybridization reaction result with high signal (MFI>100, positive/background≧5) and low background (MFI<100). As shown in FIG. 4, the detection result of CSFV SNP nested PCR product is determined by luminometer. Overload means that RLU value is over 2 million.

Example 7

Examine Clinical Samples and Calibrate the Assay System

Employing the clinical test, and using the test result to calibrate the assay system, fulfilling the high sensitivity requirements of screening CSFV clinical samples. As shown in the following table, the genotype of 100 clinical CSFV samples, which are collected from different counties in Taiwan, were determined by other methods. Those samples were applied to the present invention to testify the sensitivity of CSFV detection. The test results of clinical samples identification are shown in FIG. 5-14.

| | No. | | | | | | | | | |
|---|---|---|---|---|---|---|---|---|---|---|
| | 1 | 2 | 3 | 4 | 5 | 6 | 7 | 8 | 9 | 10 |
| Genotype | 2.1 | 2.1 | 2.1 | 2.1 | 2.1 | 2.1 | 2.1 | 2.1 | 2.1 | 2.1 |
| | No. | | | | | | | | | |
| | 11 | 12 | 13 | 14 | 15 | 16 | 17 | 18 | 19 | 20 |
| Genotype | 2.1 | 2.1 | 2.1 | 2.1 | 2.1 | 2.1 | 2.1 | 2.1 | 2.1 | 2.1 |
| | No. | | | | | | | | | |
| | 21 | 22 | 23 | 24 | 25 | 26 | 27 | 28 | 29 | 30 |
| Genotype | 2.1 | 2.1 | 2.1 | 2.1 | 2.1 | 2.1 | 2.1 | 2.1 | 2.1 | 2.1 |
| | No. | | | | | | | | | |
| | 31 | 32 | 33 | 34 | 35 | 36 | 37 | 38 | 39 | 40 |
| Genotype | 1.1 | 3.4 | 3.4 | 3.4 | 3.4 | 3.4 | 3.4 | 3.4 | 3.4 | 3.4 |
| | No. | | | | | | | | | |
| | 41 | 42 | 43 | 44 | 45 | 46 | 47 | 48 | 49 | 50 |
| Genotype | 3.4 | 3.4 | 3.4 | 3.4 | 3.4 | 2.1a | 2.1a | 2.1a | 3.4 | 3.4 |
| | No. | | | | | | | | | |
| | 51 | 52 | 53 | 54 | 55 | 56 | 57 | 58 | 59 | 60 |
| Genotype | 2.1 | 3.4 | 3.4 | 2.1 | 3.4 | 2.1 | 3.4 | 3.4 | 1.1 | 1.1 |
| | No. | | | | | | | | | |
| | 61 | 62 | 63 | 64 | 65 | 66 | 67 | 68 | 69 | 70 |
| Genotype | 2.2 | 2.2 | 3.4 | 3.4 | 3.4 | 3.4 | 3.4 | 1.1 | 2.1 | 2.1 |
| | No. | | | | | | | | | |
| | 71 | 72 | 73 | 74 | 75 | 76 | 77 | 78 | 79 | 80 |
| Genotype | 3.4 | 3.4 | 3.4 | 2.1 | 3.4 | 2.1 | 1.1 | 2.1 | 2.1 | 3.4 |
| | No. | | | | | | | | | |
| | 81 | 82 | 83 | 84 | 85 | 86 | 87 | 88 | 89 | 90 |
| Genotype | 1.1 | 2.1 | 3.4 | 3.4 | 2.1 | 3.4 | 1.1 | 1.1 | 1.1 | 1.1 |
| | No. | | | | | | | | | |
| | 91 | 92 | 93 | 94 | 95 | 96 | 97 | 98 | 99 | 100 |
| Genotype | 1.1 | 3.4 | 3.4 | 1.1 | 3.4 | 2.1a | 3.4 | 2.2 | 3.4 | 3.4 |

SEQUENCE LISTING

<110> CHOU, George, CHIN-SHENG

```
                         SEQUENCE LISTING

<160> NUMBER OF SEQ ID NOS: 5

<210> SEQ ID NO 1
<211> LENGTH: 29
<212> TYPE: DNA
<213> ORGANISM: Artificial sequence
<220> FEATURE:
<223> OTHER INFORMATION: RT-PCR Forward
<220> FEATURE:
<221> NAME/KEY: misc_binding
<222> LOCATION: (1)..(29)
<223> OTHER INFORMATION: RT-PCR forward primer

<400> SEQUENCE: 1
tgttaacaat ggtttacgcc tgctgcgag                                    29

<210> SEQ ID NO 2
<211> LENGTH: 31
<212> TYPE: DNA
<213> ORGANISM: Artificial sequence
<220> FEATURE:
<223> OTHER INFORMATION: RT-PCR reverse
<220> FEATURE:
<221> NAME/KEY: misc_binding
<222> LOCATION: (1)..(31)
<223> OTHER INFORMATION: RT-PCR reverse primer

<400> SEQUENCE: 2
gtggttgact tgcctggttt cacttgcggt t                                 31

<210> SEQ ID NO 3
<211> LENGTH: 32
<212> TYPE: DNA
<213> ORGANISM: Artificial sequence
<220> FEATURE:
<223> OTHER INFORMATION: SNP nested PCR forward
<220> FEATURE:
<221> NAME/KEY: misc_binding
<222> LOCATION: (1)..(31)
<223> OTHER INFORMATION: SNP nested PCR forward

<400> SEQUENCE: 3
agaaattggc gagtaaagga ggccagatcc ta                                32

<210> SEQ ID NO 4
<211> LENGTH: 31
<212> TYPE: DNA
<213> ORGANISM: Artificial sequence
<220> FEATURE:
<223> OTHER INFORMATION: SNP nested PCR reverse
<220> FEATURE:
<221> NAME/KEY: misc_binding
<222> LOCATION: (1)..(31)
<223> OTHER INFORMATION: SNP nested PCR reverse primer

<400> SEQUENCE: 4
tctgattagt gggttccagg attacatcag c                                 31

<210> SEQ ID NO 5
<211> LENGTH: 34
<212> TYPE: DNA
<213> ORGANISM: Artificial sequence
<220> FEATURE:
```

```
<223> OTHER INFORMATION: Hybridization
<220> FEATURE:
<221> NAME/KEY: misc_binding
<222> LOCATION: (1)..(34)
<223> OTHER INFORMATION: CSFV probe

<400> SEQUENCE: 5
tagaagtgtt gtctgaccac cttacttgta ttgg                              34
```

What is claimed is:

1. A kit for detecting classical swine fever virus (CSFV), comprising
   (a) a pair of primers consisting of SEQ ID NO:1 and SEQ ID NO:2 and
   (b) a pair of SNP primers consisting of SEQ ID NO:3 and SEQ ID NO:4.

2. The kit of claim 1, which further comprises a probe of SEQ ID NO:5.

3. The kit of claim 2, wherein the probe is labeled with a magnetic particle.

4. The kit of claim 3, wherein the magnetic particle labeled on the probe is coupled by a coupling agent comprising 1-ethyl-3-(3-dimethylaminopropyl) cobodiimide (EDC).

5. A method for detecting classical swine fever virus (CSFV) by using the kit of claim 1 comprising:
   (a) providing an amplified cDNA of a sample though RT-PCR by a pair of primers consisting of SEQ ID NO:1 and SEQ ID NO:2;
   (b) discriminating the amplified cDNA of step(a) though SNP nested PCR by a pair of SNP primers consisting of SEQ ID NO:3 and SEQ ID NO:4 ; and
   (c) identifying the amplified cDNA of step(b) by electrophoresis or a probe of SEQ ID NO:5.

6. The method of claim 5, wherein the SNP primer of SEQ ID NO:3 is incompletely complementary to the amplified cDNA of step (a) thus creating incomplete complementarity.

7. The method of claim 6, wherein the incomplete complementarity to the amplified cDNA of step(a) is caused by protruding and unbinding nucleotides.

8. The method of claim 7, wherein the protruding and unbinding nucleotides form one, two or three bubbles between the un-complementary binding of the SNP primer of SEQ ID NO:3 and the amplified cDNA of step (a)and said amount of bubbles does not impede the proceeding of the SNP nested PCR of step(b).

9. The method of claim 8, wherein the SNP nested PCR amplifies 293 base pairs of CSFV by a pair of SNP primers consisting of SEQ ID NO:3 and SEQ ID NO:4 of step(b).

10. The method of claim 9, wherein the base pairs are identified by electrophoresis.

11. The method as claimed in claim 5, wherein the SNP primer of SEQ ID NO:3 is linked to biotin.

12. The method as claimed in claim 11, wherein the biotin is linked to an enzyme for luminescent substrate.

13. The method as claimed in claim 12, wherein the enzyme is horseradish peroxidase.

14. The method of claim 12, which further comprises measuring luminescence by adding luminescent substrate.

15. A method for differentiating an infectious strain from a vaccine strain by using the kit of claim 1 comprising:
   (a) providing an amplified cDNA of a sample through RT-PCR by a pair of primers consisting of SEQ ID NO:1 and SEQ ID NO:2, wherein the pair of primers share the same template from the infectious and vaccine strains;
   (b) discriminating the amplified cDNA of step (a) through SNP nested PCR by a pair of SNP primers consisting of SEQ ID NO:3 and SEQ ID NO:4, which creates incomplete complementarity to the amplified cDNA of step (a) ; and
   (c) identifying the size of the amplified cDNA of step (b) by electrophoresis or a probe of SEQ ID NO:5 hybridized with the amplified cDNA of step (b) from the infectious strain or the vaccine strain.

16. The method of claim 15, wherein the incomplete complementarity to the amplified cDNA of step (a) is caused by protruding and unbinding nucleotides.

17. The method of claim 16, wherein the protruding and unbinding nucleotides form one, two or three bubbles between the un-complementary binding of the SNP primer and the amplified cDNA of the infectious strain of step (a) and said amount of bubbles does not impede the proceeding of the SNP nested PCR of step (b).

18. The method of claim 16, wherein the protruding and unbinding nucleotides form three bubbles between the un-complementary binding of the SNP primer and the amplified cDNA of the vaccine strain of step (a) and said amount of bubbles does impede the proceeding of the SNP nested PCR of step (b).

* * * * *